United States Patent
Yamashita et al.

(10) Patent No.: US 11,836,288 B2
(45) Date of Patent: Dec. 5, 2023

(54) DISTANCE ESTIMATION DEVICE, DISTANCE ESTIMATION METHOD AND DISTANCE ESTIMATION PROGRAM

(71) Applicant: Nippon Telegraph and Telephone Corporation, Tokyo (JP)

(72) Inventors: Jumpei Yamashita, Musashino (JP); Hidetaka Koya, Musashino (JP); Hajime Nakajima, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 0 days.

(21) Appl. No.: 17/614,189

(22) PCT Filed: May 31, 2019

(86) PCT No.: PCT/JP2019/021856
§ 371 (c)(1),
(2) Date: Nov. 24, 2021

(87) PCT Pub. No.: WO2020/240864
PCT Pub. Date: Dec. 3, 2020

(65) Prior Publication Data
US 2022/0244778 A1    Aug. 4, 2022

(51) Int. Cl.
*G06F 3/01* (2006.01)
*G01P 13/00* (2006.01)
*G01P 15/00* (2006.01)

(52) U.S. Cl.
CPC .............. *G06F 3/013* (2013.01); *G01P 13/00* (2013.01); *G01P 15/00* (2013.01); *G06F 3/012* (2013.01)

(58) Field of Classification Search
CPC ........ G06F 3/0131; G06F 3/012; G06F 3/013; G01P 13/00; G01P 15/00; G01C 3/06; A61B 3/113
See application file for complete search history.

(56) References Cited

U.S. PATENT DOCUMENTS

| 6,545,650 B1* | 4/2003 | Yamada | G02B 30/24 |
| | | | 348/E9.026 |
| 2010/0165093 A1* | 7/2010 | Sugio | A61B 3/113 |
| | | | 348/78 |
| 2013/0241805 A1* | 9/2013 | Gomez | G06F 3/013 |
| | | | 345/8 |

(Continued)

FOREIGN PATENT DOCUMENTS

JP    H09038037    2/1997

OTHER PUBLICATIONS

Bulling et al., "Eyewear Computers for Human-Computer Interaction," Interactions ACM, 2016, 4 pages.

(Continued)

*Primary Examiner* — Mihir K Rayan
(74) *Attorney, Agent, or Firm* — Fish & Richardson P.C.

(57) ABSTRACT

A distance estimation apparatus includes processing circuitry configured to acquire a sensor value output from a sensor configured to measure a relative motion of a head or eyeballs of a user who visually searches for a target on a plane and estimate a distance between the user and a search target plane using a maximum value of an amount of change when a rate of change in the sensor value acquired within a time period that is equal to or greater than a predetermined threshold value becomes a maximum.

12 Claims, 9 Drawing Sheets

(56) References Cited

U.S. PATENT DOCUMENTS

2017/0148215 A1* 5/2017 Aksoy .................. G02B 27/017

OTHER PUBLICATIONS

Kumada et al., "The Properties of Functional Visual Fields on Visual Search: Evidence from Manual Reaction Time and Saccadic Eye Movement," The Japanese Journal of Psychonomic Science, 1995, 14(2):75-85 (English Abstract).
Nakashima et al., "The Effect of Head Direction for Visual Search," Technical Report on Attention and Cognition, 2012, 15: 2 pages (English Abstract).

* cited by examiner

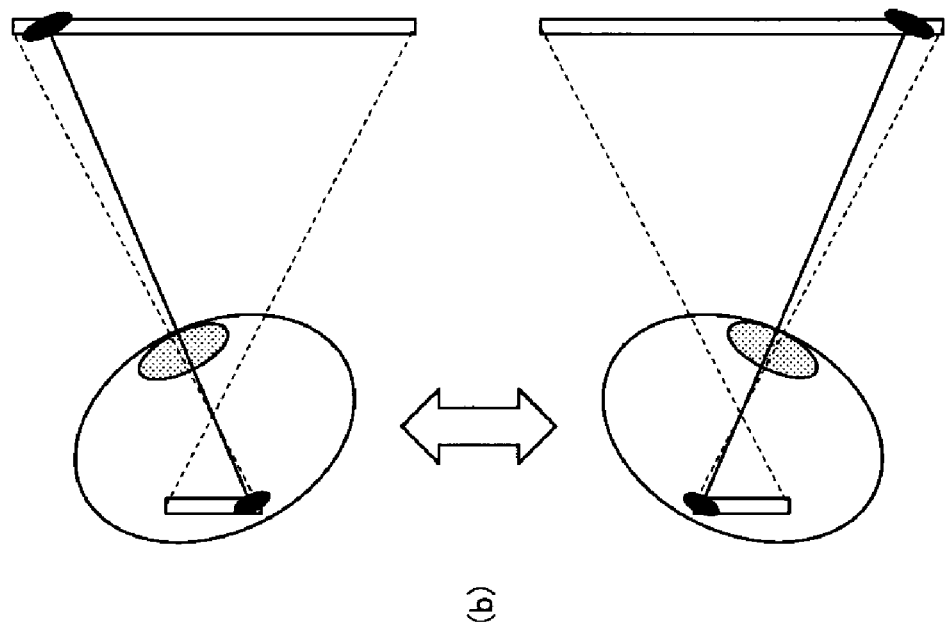
(b)
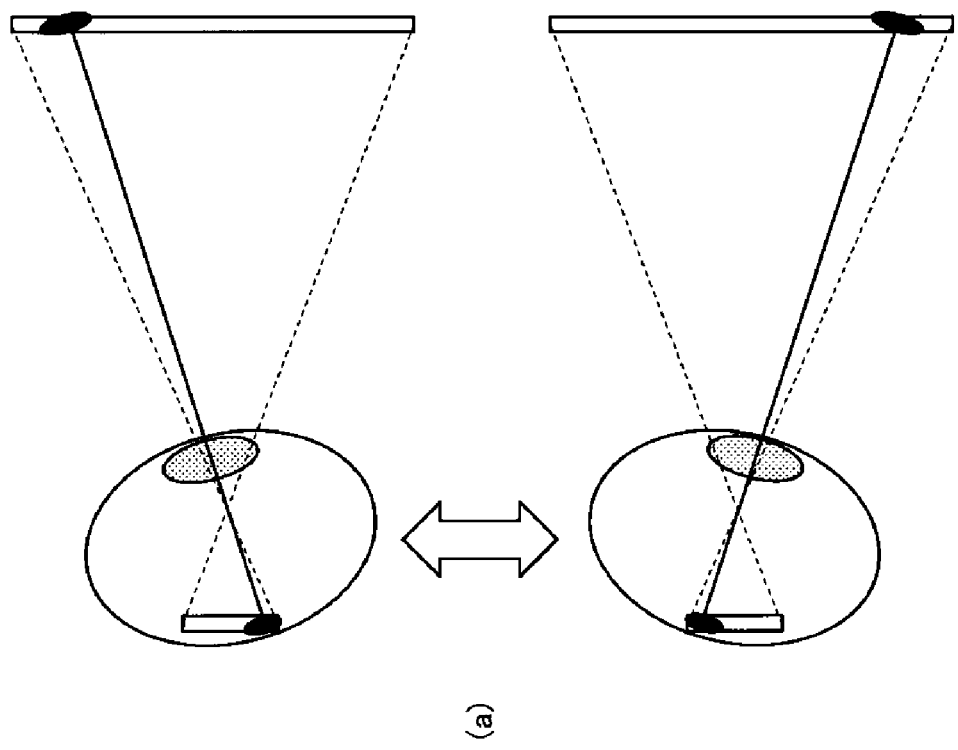
(a)
Fig. 5

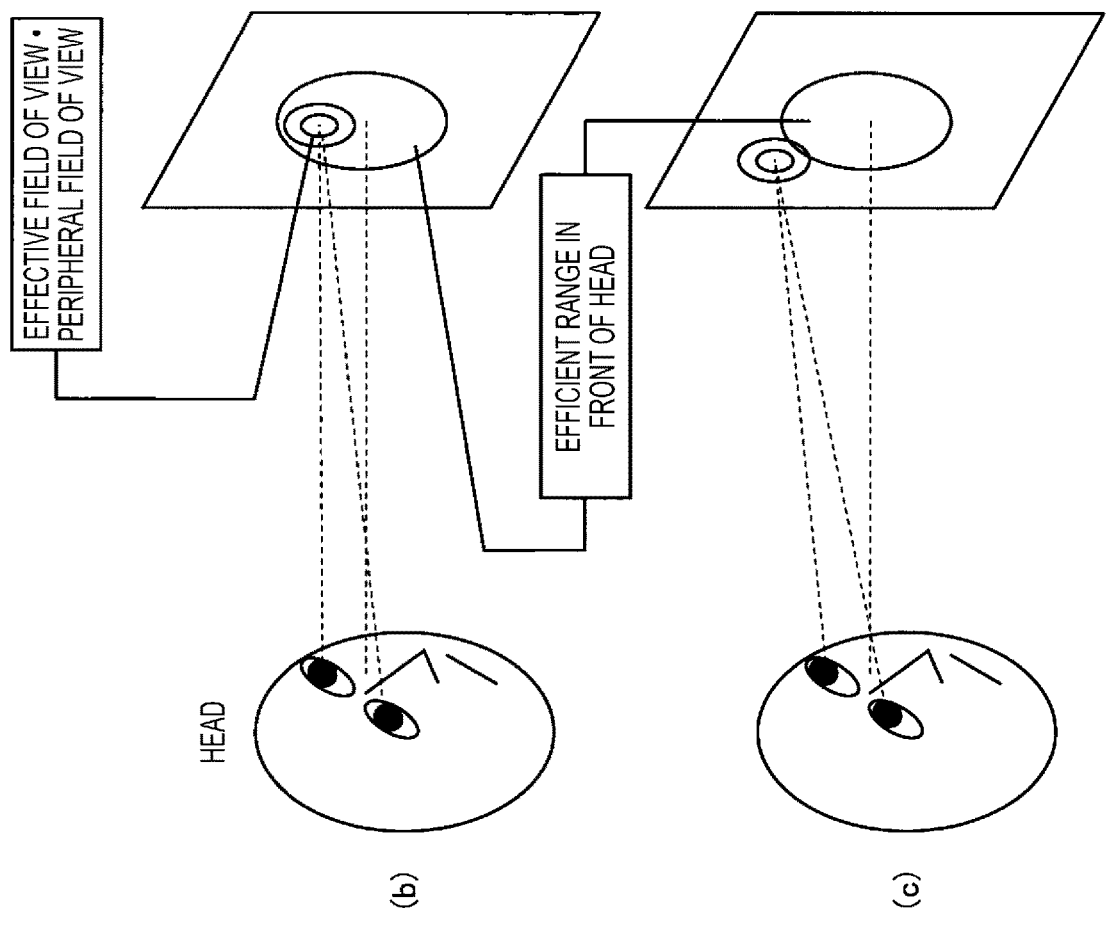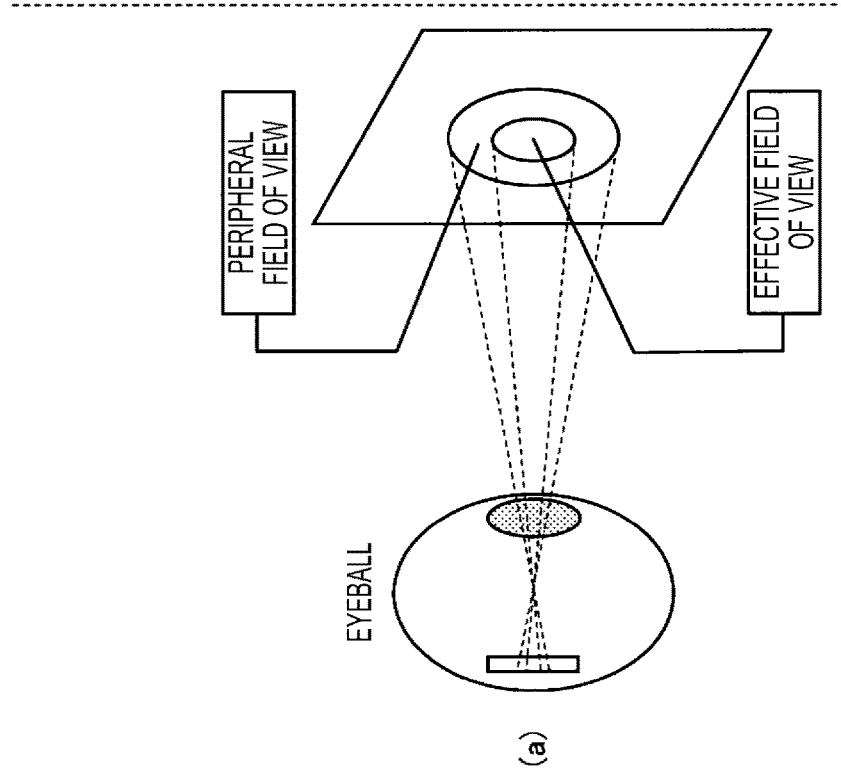
Fig. 6

DISTANCE ESTIMATION DEVICE, DISTANCE ESTIMATION METHOD AND DISTANCE ESTIMATION PROGRAM

CROSS-REFERENCE TO RELATED APPLICATIONS

This application is a National Stage application under 35 U.S.C. § 371 of International Application No. PCT/JP2019/021856, having an International Filing Date of May 31, 2019, the disclosure of which is considered part of the disclosure of this application, and is incorporated in its entirety into this application.

TECHNICAL FIELD

The present invention relates to a distance estimation apparatus, a distance estimation method, and a distance estimation program.

BACKGROUND ART

It may be important to acquire a distance between a user and a search target plane (hereinafter, also referred to as a search plane or a target plane in some cases) when the user visually searches for a target on the plane. For example, it is important to acquire the distance between the user and the target plane when a sensor device analyzes an action in which the user in a seated position operates an IT device through visual information presented on a display or an action in which the user stands and views a poster or a picture. Also, to estimate a position at which the user is gazing, that is, a gaze point in the target plane through measurement of the motion of the eyeballs, it is necessary to acquire the distance as an assumption since the amount of movement of the gaze point in the target plane changes in accordance with the distance between the user and the target plane.

In recent years, techniques using wearable devices that users can wear on their heads on a daily basis have been widely used. For example, various wearable devices capable of acquiring information on the surroundings of the eyeballs of users have been proposed (see Non Patent Literature 1). Thus, techniques for estimating distances between the heads of users and search target planes using information acquired from wearable devices have been expected.

Note that Patent Literature 1 discloses a technique for estimating the size of an effective field of view from the motion of eyeballs. Moreover, Non Patent Literature 2 describes the motion of eyeballs in visual searching. In addition, Non Patent Literature 3 describes an efficient range in front of a head.

CITATION LIST

Patent Literature

Patent Literature 1: Japanese Laid-open Patent Publication No. 09-38037 A

Non Patent Literature

Non Patent Literature 1: Andreas Bulling, Kai Kunze, "Eyewear Computers for Human-Computer Interaction", INTERACTIONS, ACM, 2016
Non Patent Literature 2: Kumada and two others, "The Properties of Functional Visual Fields on Visual Search: Evidence from Manual Reaction Time and Saccadic Eye Movement", The Japanese Journal of Psychonomic Science, 1995, Vol. 14, No. 2, p. 75 to 85
Non Patent Literature 3: Nakajima, Shioiri, "Effect of Head Direction on Visual Searching", Technical Report on Attention and Cognition, 2012, No. 15

SUMMARY OF THE INVENTION

Technical Problem

However, according to the related art, it is difficult to accurately estimate the distance between a user and a search target plane in a case in which the user visually searches for a target on the plane. For example, estimation of the distance between a user and a target using a wearable device can be only performed in a case in which the wearable device includes a special sensor using light/sound waves or a camera configured to image a user's facing direction. Moreover, in a case in which the camera configured to image the user's facing direction is attached to the head of the user, the captured image may be significantly blurred. Thus, using the image as an information source for estimating the distance requires special techniques and is difficult (see Non Patent Literature 1).

The present invention has been made in view of such circumstances, and an object thereof is to accurately estimate the distance between a user and a search target plane in a case in which the user visually searches for a target on the plane.

Means for Solving the Problem

In order to solve the aforementioned problem and achieve the object, a distance estimation apparatus according to the present invention includes: processing circuitry configured to acquire a sensor value output from a sensor configured to measure a relative motion of a head or eyeballs of a user who visually searches for a target on a plane; and estimate a distance between the user and a search target plane using a maximum value of an amount of change when a rate of change in the sensor value acquired within a time period that is equal to or greater than a predetermined threshold value becomes a maximum.

Effects of the Invention

According to the present invention, it is possible to accurately estimate the distance between a user and a target plane in a case in which the user visually searches for a target on a plane.

BRIEF DESCRIPTION OF DRAWINGS

FIG. 5 is a diagram for explaining processing of the estimation unit.
FIG. 6 is a diagram for explaining relative motions of the head and eyeballs.

DESCRIPTION OF EMBODIMENTS

Hereinafter, an embodiment of the present invention will be described in detail with reference to the drawings. Note that the present invention is not limited by the embodiment. Note that in description of the drawings, the same components are denoted by the same reference signs.

Configuration of Distance Estimation Apparatus

Figure 1:
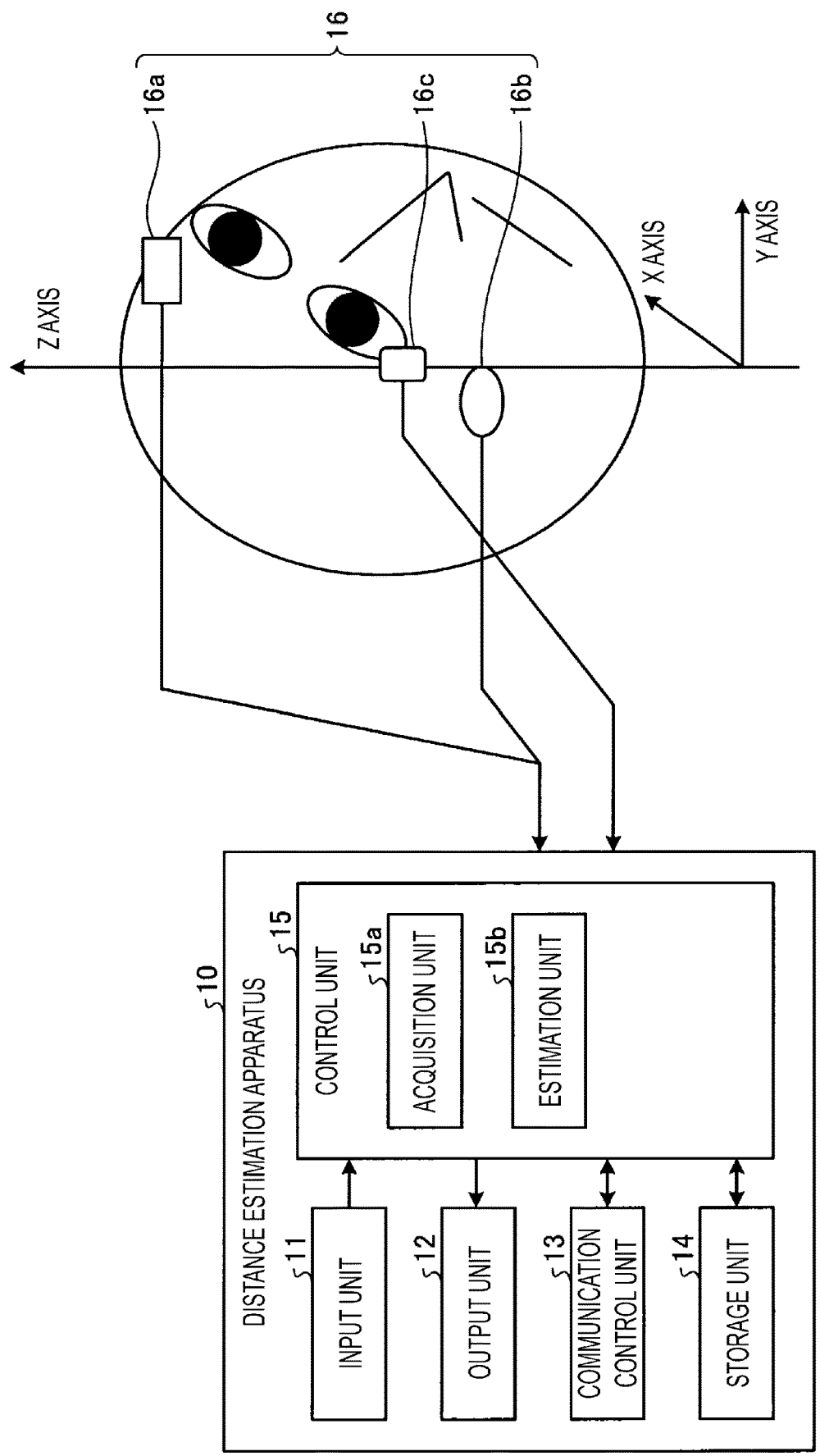
FIG. 1 is a schematic diagram illustrating, as an example, an overview configuration of a distance estimation apparatus according to a present embodiment.

FIG. 1 is a schematic view illustrating, as an example, an overview configuration of a distance estimation apparatus according to the present embodiment. As illustrated in FIG. 1 as an example, a distance estimation apparatus 10 according to the present embodiment is implemented by a general-purpose computer such as a PC and includes an input unit 11, an output unit 12, a communication control unit 13, a storage unit 14, a control unit 15, and sensors 16.

The input unit 11 is implemented using an input device such as a keyboard or a mouse and inputs various kinds of instruction information for starting processing to the control unit 15 in response to an operation input by an operator. The output unit 12 is implemented by a display device such as a liquid crystal display or a printing device such as a printer. For example, the output unit 12 displays a result of distance estimation processing, which will be described below.

The sensors 16 measure a relative motion of a head or eyeballs of a user who visually searches for a target on a plane. Specifically, the sensors 16 measure an acceleration of the head, an amount of rotation of the head, or an ocular potential. FIG. 1 illustrates, as examples of the sensors 16 configured to measure a relative motion of the head, an acceleration sensor 16a configured to measure the acceleration of the head and a rotation amount sensor 16b configured to measure the amount of rotation of the head. Also, an ocular potential meter 16c configured to measure the ocular potential is illustrated as an example of the sensors 16 configured to measure a relative motion of the eyeballs.

Figure 2:
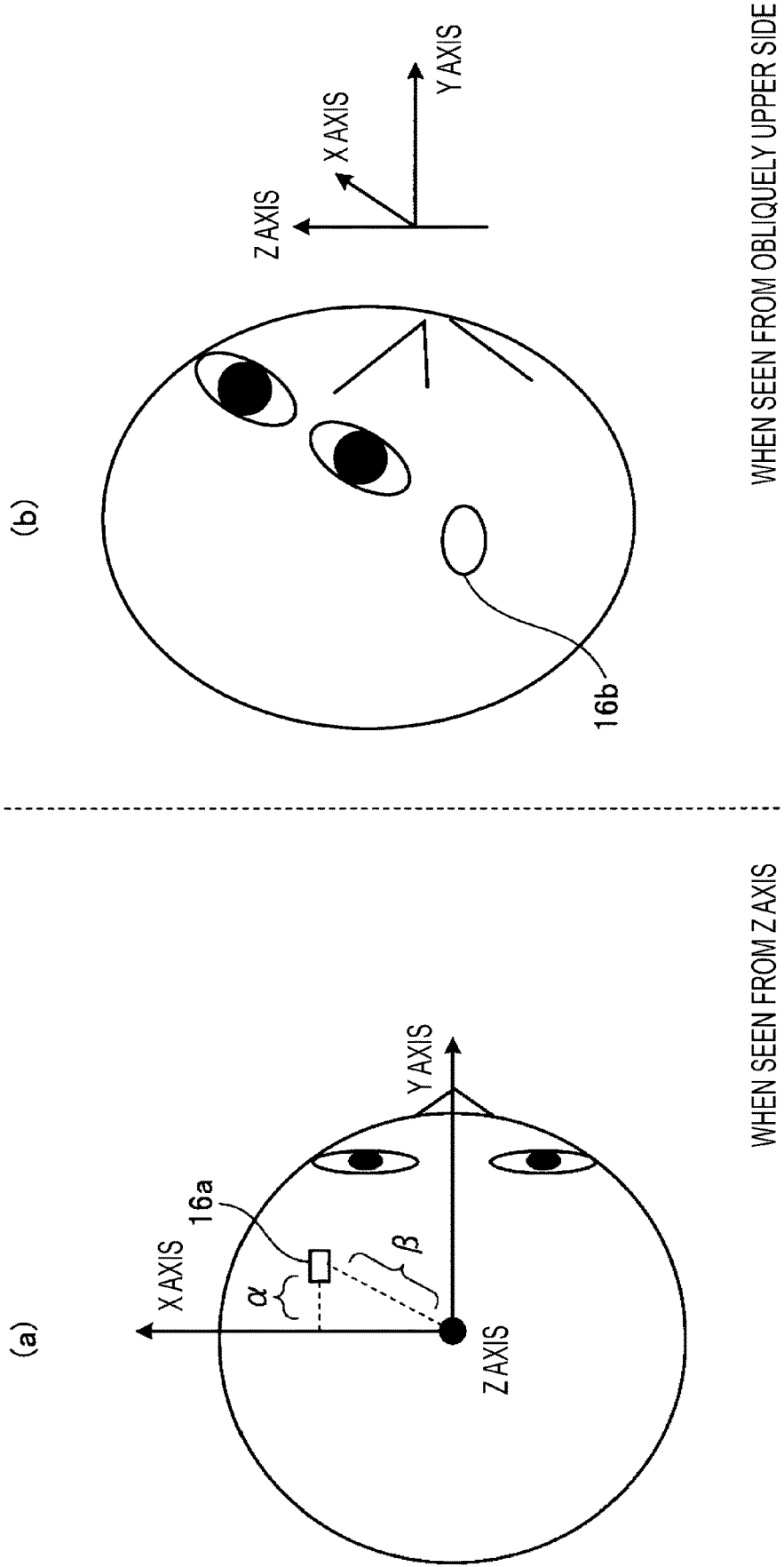
FIG. 2 is a diagram illustrating, as an example, a sensor configured to measure relative motions of a head.

Here, FIG. 2 is a diagram illustrating, as an example, the sensors 16 configured to measure a relative motion of the head. FIG. 2(a) illustrates, as an example, the acceleration sensor 16a configured to measure acceleration of the head. In FIG. 2(a), the amount of relative motion (acceleration) that reflects rotation of the head in the up-down direction (about an X axis) is measured by the acceleration sensor 16a attached at a position with a coordinate value α that is equal to or greater than zero on a Y axis representing the front-back direction of the head. Also, the amount of relative motion (acceleration) that reflects rotation of the head in the left-right direction (about a Z axis) is measured by the acceleration sensor 16a attached to a position with a coordinate value β that is not zero on either the Y axis or the X axis where the coordinates on the Y axis and the X axis that perpendicularly intersect the Z axis representing the up-down direction of the head are zero.

In addition, FIG. 2(b) illustrates, as an example, the rotation amount sensor 16b configured to measure the amount of rotation of the head. The rotation amount sensor 16b can measure the amount of relative motion (the amount of rotation) that reflects rotation of the head in the up-down direction and the left-right direction regardless of the position where the rotation amount sensor 16b is attached.

Also, the ocular potential meter 16c configured to measure a relative motion of the eyeballs is implemented by an ElectroOculoGraphy (EOG) method, for example. According to the EOG method, electrodes are attached to the periphery of the eyeballs, and a motion direction and the amount of motion of the eyeballs are estimated from changes in potential using the fact that the eyeballs have a positive potential on the front side and a negative potential on the rear side. According to an AC EOG method (hereinafter, this will be simply referred to as an EOG method), only the amount of change in potential in the periphery of the eyeballs is acquired in order to curb noise called drift, and information related to a relative motion of the eyeballs is acquired. When electrodes are attached immediately above and immediately below the eyeballs to measure the potentials, and the potentials immediately above the eyeballs increase while the potentials immediately below the eyeballs decrease, for example, upward changes in the front sides of the eyeballs, that is, upward movement of a line of sight is estimated.

Note that either the sensor 16 configured to measure a relative motion of the head or the sensor 16 configured to measure a relative motion of the eyeballs may be provided. In other words, it is only necessary to include one or more of the sensors 16 configured to measure any of the acceleration of the head, the amount of rotation of the head, and the ocular potential.

Moreover, the sensors 16 may not be included in the distance estimation apparatus 10. In such a case, the distance estimation apparatus 10 acquires sensor values from an information terminal provided with the sensors 16, a management apparatus configured to manage sensor values output from the sensors 16, or the like prior to the distance estimation processing, which will be described later.

FIG. 1 is referred to again for description. The communication control unit 13 is implemented by a network interface card (NIC) or the like and controls communication between the control unit 15 and an external apparatus via an electric communication line such as a local area network (LAN) or the Internet. For example, the communication control unit 13 controls communication between the control unit 15 and the information terminal provided with the sensors 16, and the management device configured to manage the sensor values output from the sensors 16.

The storage unit 14 is implemented by a semiconductor memory element such as a random access memory (RAM) or a flash memory or a storage device such as a hard disk or an optical disc. The storage unit 14 stores a processing program that causes the distance estimation apparatus 10 to operate and data and the like used during execution of the processing program in advance or temporarily every time processing is performed. Note that the storage unit 14 may be configured to communicate with the control unit 15 via the communication control unit 13.

In the present embodiment, the storage unit 14 stores the sensor values output from the sensors 16, for example. The sensor values are collected by an acquisition unit 15a, which will be described later, and then stored in the storage unit 14 prior to the distance estimation processing described below.

Note that the present embodiment is not limited to the case in which the sensor values are stored in the storage unit 14 and the sensor values may be collected when the distance estimation processing is executed. In such a case, the acquisition unit 15a collects the sensor values prior to the processing of an estimation unit 15b, which will be described later.

The control unit 15 is implemented using a central processing unit (CPU) or the like and executes the processing program stored in the memory. The control unit 15 thus functions as the acquisition unit 15a and the estimation unit 15b as illustrated in FIG. 1 as an example. Note that these functional units may be implemented on different pieces of hardware. Also, the control unit 15 may include other functional units.

The acquisition unit 15a acquires the sensor values output from the sensors 16 configured to measure a relative motion of the head or the eyeballs of the user who visually searches for a target on a plane. Note that in a case in which the sensors 16 are included in an apparatus outside the distance estimation apparatus 10, the acquisition unit 15a acquires the sensor values from the information terminal provided with the sensors 16, the management apparatus configured to manage the sensor values output from the sensors 16, or the like via the input unit 11 or the communication control unit 13. The acquisition unit 15a may cause the storage unit 14 to store the acquired sensor values.

The estimation unit 15b estimates the distance between the user and the search target plane using a maximum value of the amount of change when a rate of change in the sensor value acquired within a time period that is equal to or greater than a predetermined threshold value becomes a maximum. In such a case, the estimation unit 15b estimates the distance using values related to the user's searching action among the sensor values. In other words, the estimation unit 15b removes the sensor values at timings other than the user's searching action from the acquired sensor values and uses the remaining sensor values for estimating the distance.

Figure 3:
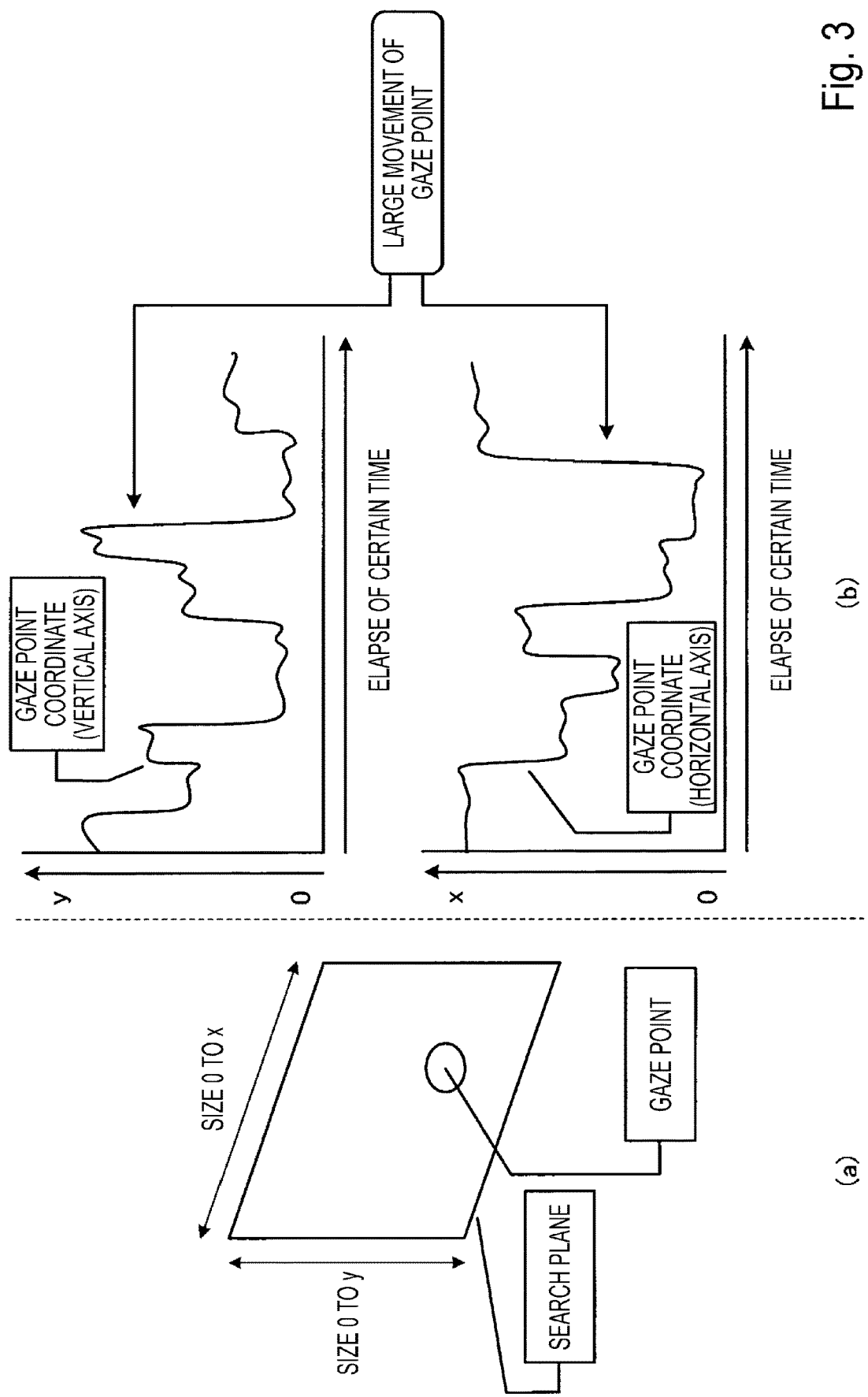
FIG. 3 is a diagram for explaining processing of an estimation unit.
Figure 4:
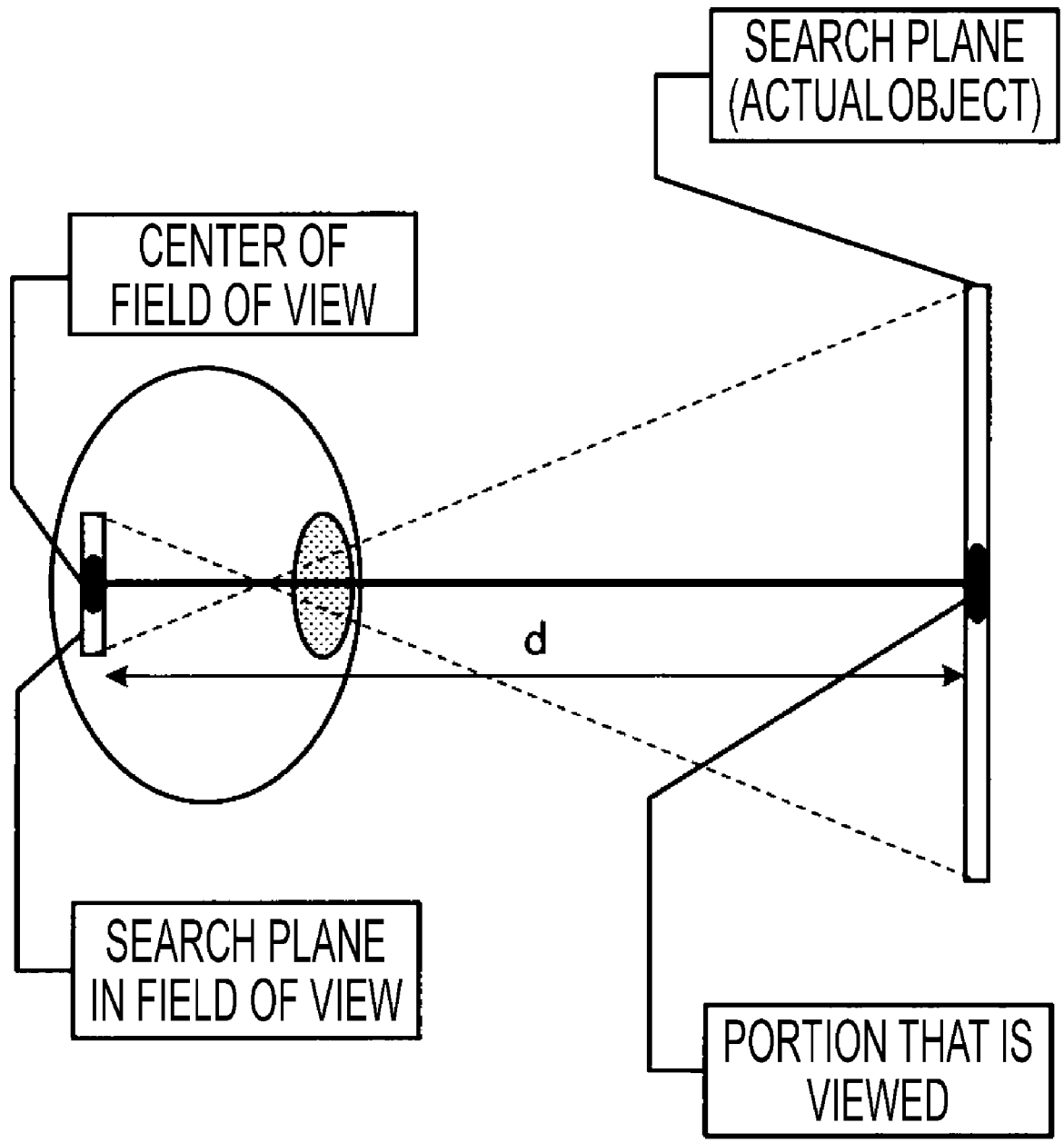
FIG. 4 is a diagram for explaining processing of the estimation unit.

Here, FIGS. 3 to 5 are diagrams for explaining processing of the estimation unit 15b. The sensor values output from the sensors 16 represent the gaze point in the user's field of view, that is, the position at which the user is gazing. Also, the range of the user's searching action on the target plane, that is, the range in which the gaze point is present is limited to the size of the target plane. In addition, it is assumed that the user gazes at the entire target plane up to the vicinities of the ends thereof at least once before elapse of a certain time after the start of the searching.

Thus, the amount of the motion of the head or the motion of the eyeballs when the user moves the gaze point greatly in the up-down direction and the left-right direction is substantially identical to or is at least proportional to the size of the target plane in the user's field of view. Thus, the estimation unit 15b can estimate the size of the search plane in the user's field of view using the amount of the "large movement of the gaze point" before elapse of the certain time after the user starts searching, as illustrated in FIG. 3(b).

For example, the estimation unit 15b may regard, as the size of the search plane in the user's field of view, the amount of the "large movement of the gaze point" before the elapse of the certain time, that is, within a time period that is equal to or greater than a predetermined threshold value. Here, the predetermined threshold value is set in view of a situation the estimation unit may be employed. Also, the amount of the "large movement of the gaze point" can be said to be the maximum value of the amount of change when the rate of change in the sensor value becomes a maximum.

Note that in the example illustrated in FIG. 3, the sensor value is represented by xy coordinate values in the search plane in the user's field of view as illustrated in FIG. 3(a). Also, FIG. 3(b) illustrates, as an example, temporal change in the coordinate value of the gaze point on the x axis in the horizontal direction and a temporal change in the coordinate value on the y axis in the vertical direction.

Also, as the size of the search plane in the field of view increases, the distance d between the head or the eyeballs (the eyeballs in the example illustrated in FIG. 4) and the search plane decreases, as illustrated in FIG. 4. Also, as the distance between the head or the eyeballs of the user and the search plane increases, the amount of motion of the head or the eyeballs (rotation angle in FIG. 5) decreases, as illustrated in FIG. 5(a). Also, as the distance between the head or the eyeballs of the user and the search plane decreases, the amount of motion of the head or the eyeballs increases, as illustrated in FIG. 5(b).

Thus, the estimation unit 15b can relatively estimate the distance d between the user and the search plane using the estimated size of the search plane in the user's field of view. For example, when distances d are different in a plurality of situations, the estimation unit 15d can estimate which distance is longer or shorter than the others or which region is at a relatively short distance or a relatively long distance.

The estimation unit 15b can further estimate an absolute value of the distance between the user and the search target plane using the size of the search target plane. In other words, the estimation unit 15b can calculate an absolute value of the distance d between the user and the search plane from a ratio between the size of the search plane (actual object) and the size of the search plane in the field of view as illustrated in FIG. 4.

In this manner, the estimation unit 15b estimates the distance between the user and the target plane using a condition unique to the search in the target plane that the amount of movement of the user's gaze point is proportional to the size of the target plane in the field of view within a certain time range.

Note that in a case in which the sensors 16 measure relative motions of the head and the eyeballs, the estimation unit 15b estimates the distance between the user and the target plane by a different processing method in accordance with whether or not there is a relative motion of the head or whether or not the relative motion of the head precedes a relative motion of the eyeballs in a relative motion corresponding to the maximum value. In this manner, the estimation unit 15b can more accurately estimate the distance between the user and the target plane.

Specifically, in a case in which there is a relative motion of the head and the relative motion of the head precedes a relative motion of the eyeballs in a relative motion corresponding to the maximum value, the estimation unit 15b estimates the distance using a total value of the sensor value of the relative motion of the head and the sensor value of the relative motion of the eyeballs. Also, in a case in which there is a relative motion of the head and the relative motion of the head does not precede a relative motion of the eyeballs, the estimation unit 15b estimates the distance using an average value obtained by applying predetermined weights to the sensor value of the relative motion of the head and the sensor value of the relative motion of the eyeballs. Moreover, in a case in which there is no relative motion of the head, the estimation unit 15b estimates the distance using the sensor value of the relative motion of the eyeballs.

Here, FIG. 6 is a diagram for explaining relative motions of the head and the eyeballs. First, the effective field of view in FIG. 6(a) is a given range from the center of the eye socket in which semantic information can be collected. If an object departs from the effective field of view, the user cannot perform semantic information processing of the object. Also, the peripheral field of view is a range outside the effective field of view in which semantic processing of an object cannot be performed but the presence of the object can be detected, that is, a range in which the position information can be detected (see Non Patent Literatures 1 and 2).

In each of FIGS. 6(b) and 6(c), the efficient range in front of the head is a given range from the center in the direction that the head faces in which it is possible to perform information processing (see Non Patent Literature 3). Even if an object is at a position outside the efficient range in front of the head as illustrated in FIG. 6(c), it is possible to perform semantic processing of information and detection of position information as long as the object is included in the effective field of view or the peripheral field of view, although efficiency of the information processing is degraded.

Also, if the object is located close to the position at which the user is currently gazing and is included within the effective field of view without moving the gaze point, a motion of eyeballs (saccade) does not occur. On the other hand, if the object is located a bit far from the position at which the user is currently gazing and is included in the peripheral field of view immediately outside the effective field of view, the user plans and executes a motion of the eyeballs to include the object within the range of the effective field of view. At this time, in a case in which the motion of the eyeballs is large and the gaze point moves to the outside of the efficient range in front of the head, the user continues the motion of the head until the gaze point is included in the efficient range in front of the head. At the same time, the eyeballs are sequentially returned to the original direction by the amount corresponding to the motion of the head due to vestibuloocular reflex. If the process is completed, then the object at the gaze target is included in the effective field of view and the efficient range in front of the head.

Also, a case where the object is located further away from the position at which the user is currently gazing and is not even included in the peripheral field of view will be considered. Because any motion of the eyeballs cannot be largely corrected once the motion occurs, it is necessary to recognize the position of the object before the gaze point is moved. In other words, the user performs a motion of the head first to include the object in the peripheral field of view and then plans a motion of the eyeballs. Thus, the user performs a motion of the head in the direction of a rough position of the object, for example, through extraction from his/her memory, and immediately after the object is included in the peripheral field of view, the user performs a motion of the eyeballs. In a case in which the gaze point moves to the outside of the efficient range in front of the head at this time, then the user continuously performs the motion of the head until the gaze point is included in the efficient range in front of the head similarly to the above description.

Thus, in a case in which sensor values of both motions of the head and the eyeballs are acquired, the estimation unit 15b changes the processing to be performed on the sensor values in accordance with whether or not there is a motion of the head and which of the motion of the head and a motion of the eyeballs precedes the other, and estimates the distance between the user and the target plane.

In a region in which the distance between the user and the target plane is short, for example, the "large movement of the gaze point" in the user's field of view is movement of the gaze point from a gaze point at a certain timing toward an object outside the peripheral field of view. In such a case, the motion of the head precedes the motion of the eyeballs, and the motion of the eyeballs follows the motion of the head. The estimation unit 15b calculates the amount of the "large movement of the gaze point" in this case by adding the amount of the preceding motion of the head and the amount of the following motion of the eyeballs. Note that a larger value means a shorter distance between the user and the target plane in this region.

Also, in a region in which the distance between the user and the target plane is intermediate, the "large movement of the gaze point" in the user's field of view is movement of the gaze point from a gaze point at a certain timing toward an object in the peripheral field of view. At that time, the gaze point moves to the outside of the efficient range in front of the head. In such a case, the motion of the eyeballs precedes to the motion of the head, and the motion of the head follows the motion of the eyeballs. The amount of the "large movement of the gaze point" in this case is also equal both to the amount of the motion of the eyeballs and to the amount of the motion of the head. Thus, in this case, the estimation unit 15b calculates, as the amount of the "large movement of the gaze point", an average value obtained by applying predetermined weights to the amount of the motion of the head and the amount of the motion of the eyeballs. Any one of the weights may be set to zero. Note that a larger value means a shorter distance between the user and the target plane in this region.

Also, in a region in which the distance between the user and the target plane is long, the "large movement of the gaze point" in the user's field of view is movement of the gaze point from a gaze point at a certain timing toward an object in the peripheral field of view. At that time, the gaze point does not move to the outside of the efficient range in front of the head. In that case, no motion of the head occurs, and only a motion of the eyeballs occurs. The amount of the "large movement of the gaze point" in this case is equal to the amount of the motion of the eyeballs. Note that a larger value means a shorter distance between the user and the target plane in this region.

Note that in a case in which an absolute distance between the user and the target plane is estimated, the aforementioned three regions of the short distance, the intermediate distance, and the long distance may change in accordance with cognitive characteristics of the individual users and the user conditions. It is known that if a task load increases or a degree of awareness decreases, then the effective field of view is narrowed. Also, the sizes of the peripheral field of view and the efficient range in front of the head may also change in relation to the effective field of view.

Figure 7:
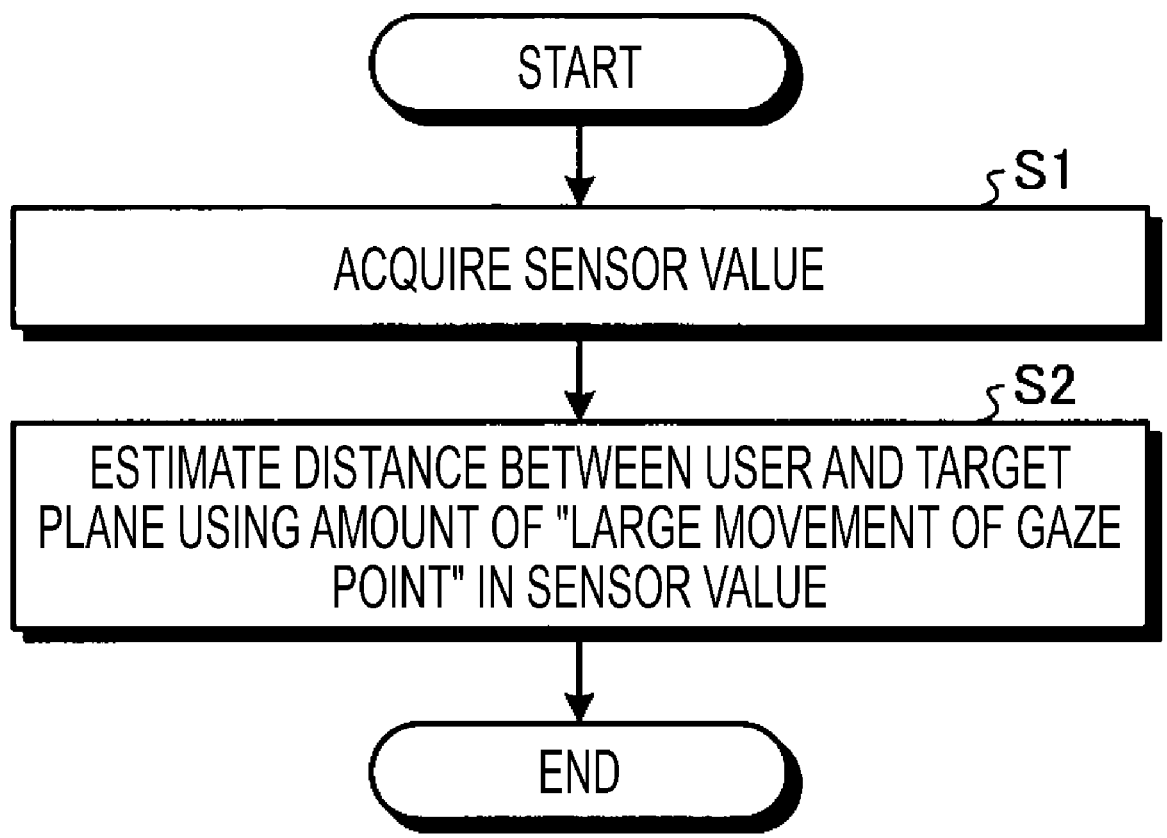
FIG. 7 is a flowchart illustrating a distance estimation processing procedure.
Figure 8:
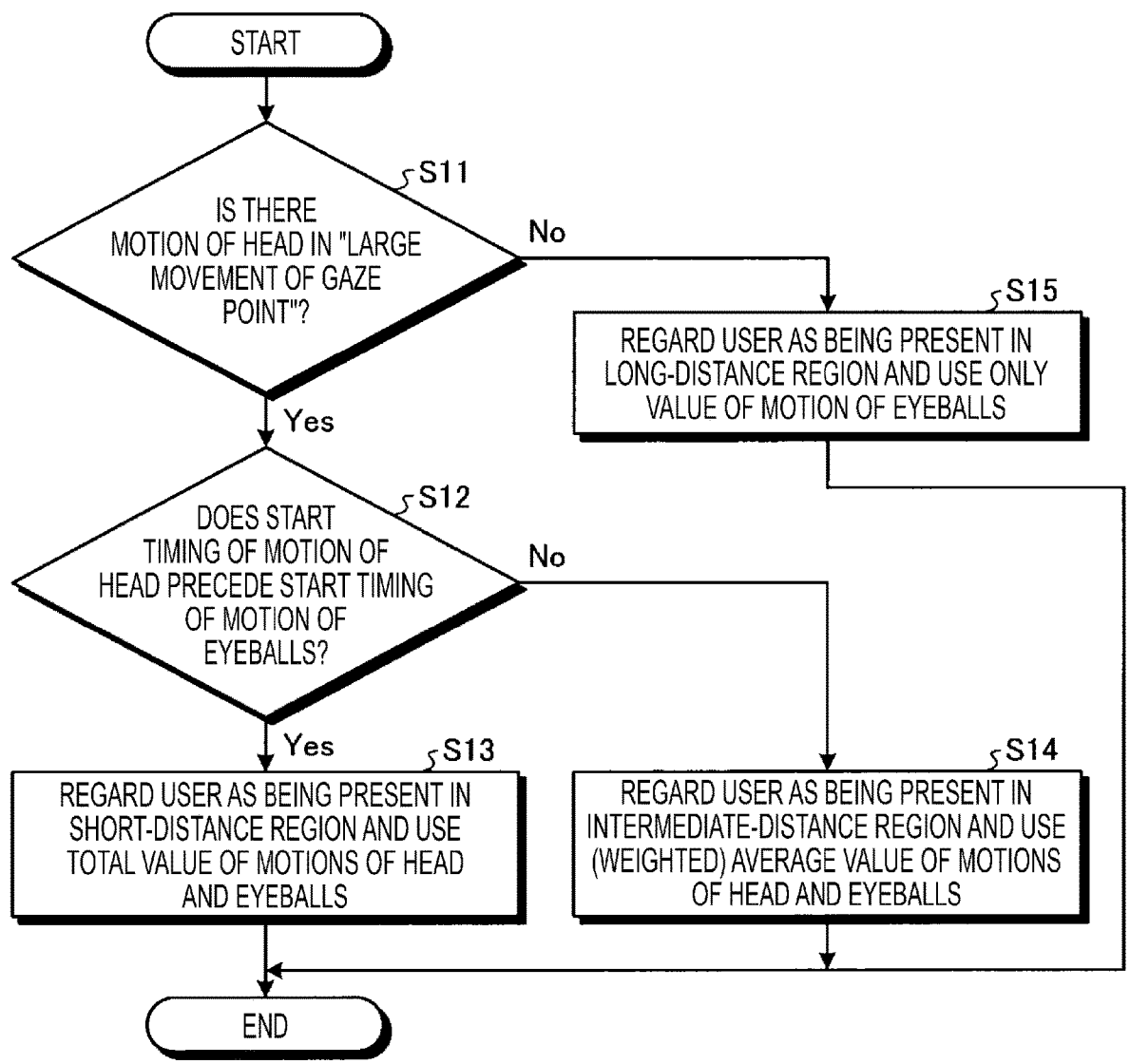
FIG. 8 is a flowchart illustrating the distance estimation processing procedure.

Thus, it is possible to further accurately estimate the distance between the user and the target plane by separately calculating the sizes of the user's effective field of view, the peripheral field of view, and the efficient range in front of the head (see Patent Literature 1) and performing estimation again in accordance with the changes thereof Distance Estimation Processing Next, distance estimation processing performed by the distance estimation apparatus 10 according to the present embodiment will be described with reference to FIGS. 7 and 8. FIGS. 7 and 8 are flowcharts illustrating procedures for the distance estimation processing. First, the flowchart in FIG. 7 is started at a timing at which the user inputs an operation for providing a start instruction, for example.

First, the acquisition unit 15a acquires sensor values output from the sensors 16 configured to measure the relative motion of the head or the eyeballs of the user who visually searches for a target on a plane (Step S1).

Also, the estimation unit 15b estimates the distance between the user and the search target plane using the amount of the "large movement of the gaze point", that is, the maximum value of the amount of change when the rate of change becomes the maximum from among the sensor values acquired within a time period that is equal to or greater than the predetermined threshold value (Step S2). In this manner, the series of distance estimation processing operations end.

Also, FIG. 8 illustrates, as an example, a procedure for determining a specific method for the processing in Step S2 described above in the case in which the sensors 16 measure relative motions of the head and the eyeballs. The flowchart in FIG. 8 is started at a timing at which the estimation unit 15b acquires sensor values of both motions of the head and the eyeballs, for example.

The estimation unit 15b checks whether or not there is a motion of the head in the "large movement of the gaze point (Step S11). In a case in which there is a motion of the head (Step S11; Yes), the estimation unit 15b proceeds the processing to Step S12.

In the processing in Step S12, the estimation unit 15b checks whether or not the motion of the head precedes a motion of the eyeballs. In a case in which the motion of the head precedes the motion of the eyeballs (Step S12; Yes), the estimation unit 15b regards the user as being present in the short-distance region and estimates the distance using a total value of the sensor value of the motion of the head and the sensor value of the motion of the eyeballs (Step S13).

On the other hand, in a case in which the motion of the head does not precede the motion of the eyeballs (Step S12; No), the estimation unit 15b regards the user as being present in the intermediate-distance region and estimates the distance using an average value obtained by applying predetermined weights to the sensor value of the motion of the head and the sensor value of the motion of the eyeballs (Step S14).

Also, in a case in which there is no motion of the head (Step S11; No), the estimation unit 15b regards the user as being present in the long-distance region and estimates the distance using the sensor value of the motion of the eyeballs (Step S15).

As described above, in the distance estimation apparatus 10 according to the present embodiment, the acquisition unit 15a acquires the sensor values output from the sensors 16 configured to measure the relative motion of the head or the eyeballs of the user who visually searches for the target on the plane. Also, the estimation unit 15b estimates the distance between the user and the search target plane using the maximum value of the amount of change when the rate of change in the sensor values acquired within a time period that is equal to or greater than the predetermined threshold value becomes a maximum.

This enables the distance estimation apparatus 10 to automatically estimate the distance between the head of the user who performs an operation and the target plane using the lightweight and inexpensive sensors 16. At this time, there is no need of a calibration procedure such as asking the user to direct the center of the head to four ends of the target plane. In the related art, a camera captures, from the front side, an image of a situation in which the user is performing visual search on the target plane, for example, to estimate the distance between the user and the target plane. However, in many cases, no camera is attached on the side of the target plane, and a camera attached on the user's side is heavy and expensive and is directed to the user to analyze actions of the user. Thus, it is difficult to obtain such an image. In contrast, the distance estimation apparatus 10 according to the present embodiment does not need the image of the situation in which the user is performing visual search on the target plane, which is captured by a camera from the front side.

Also, the acceleration sensor 16a configured to measure the relative motion of the head measures a rate of change in the speed per unit time of a parallel motion of the head of the user. Then, the rotation amount sensor 16b measures the amount of rotation about an axis of the head of the user. The sensor values output from these sensors 16 are the amounts of change in the relative position of the head of the user. Although it is possible to calculate the position of the head at a clock time t from the position at the clock time 0 by adding the amounts of change in a time series manner, the accuracy thereof is low due to accumulated errors. In contrast, the distance estimation apparatus 10 according to the present embodiment can accurately estimate the distance with no errors accumulated using a condition unique to the search on the target plane that the amount of movement of the user's gaze point is proportional to the size of the target plane on the field of view in some temporal range.

In this manner, the distance estimation apparatus 10 can easily and accurately estimate the distance between the user and the search target plane.

Also, in a case in which the sensor 16 measures the relative motions of the head and the eyeballs, the estimation unit 15b estimates the distance by a different processing method in accordance with whether there is a relative motion of the head or whether the relative motion of the head precedes a relative motion of the eyeballs in a relative motion corresponding to the maximum value. In this manner, it is possible to further accurately estimate the distance between the user and the search target plane using characteristics unique to a human searching activity.

Program

It is also possible to create a program in which the processing executed by the distance estimation apparatus 10 according to the present embodiment described above is described in a computer-executable language. In one embodiment, the distance estimation apparatus 10 can be implemented by installing a distance estimation program that executes the aforementioned distance estimation processing as package software or on-line software on a desired computer. For example, it is possible to cause an information processing apparatus to function as the distance estimation apparatus 10 by causing the information processing apparatus to execute the aforementioned distance estimation program. The information processing apparatus mentioned here includes a desktop or laptop-type personal computer. Furthermore, as other examples, a mobile communication terminal such as a smartphone, a mobile phone, or a personal handyphone system (PHS), a slate terminal such as a personal digital assistant (PDA), and the like are included in the category of the information processing apparatus. Also, the functions of the distance estimation apparatus 10 may be implemented in a cloud server.

Figure 9:
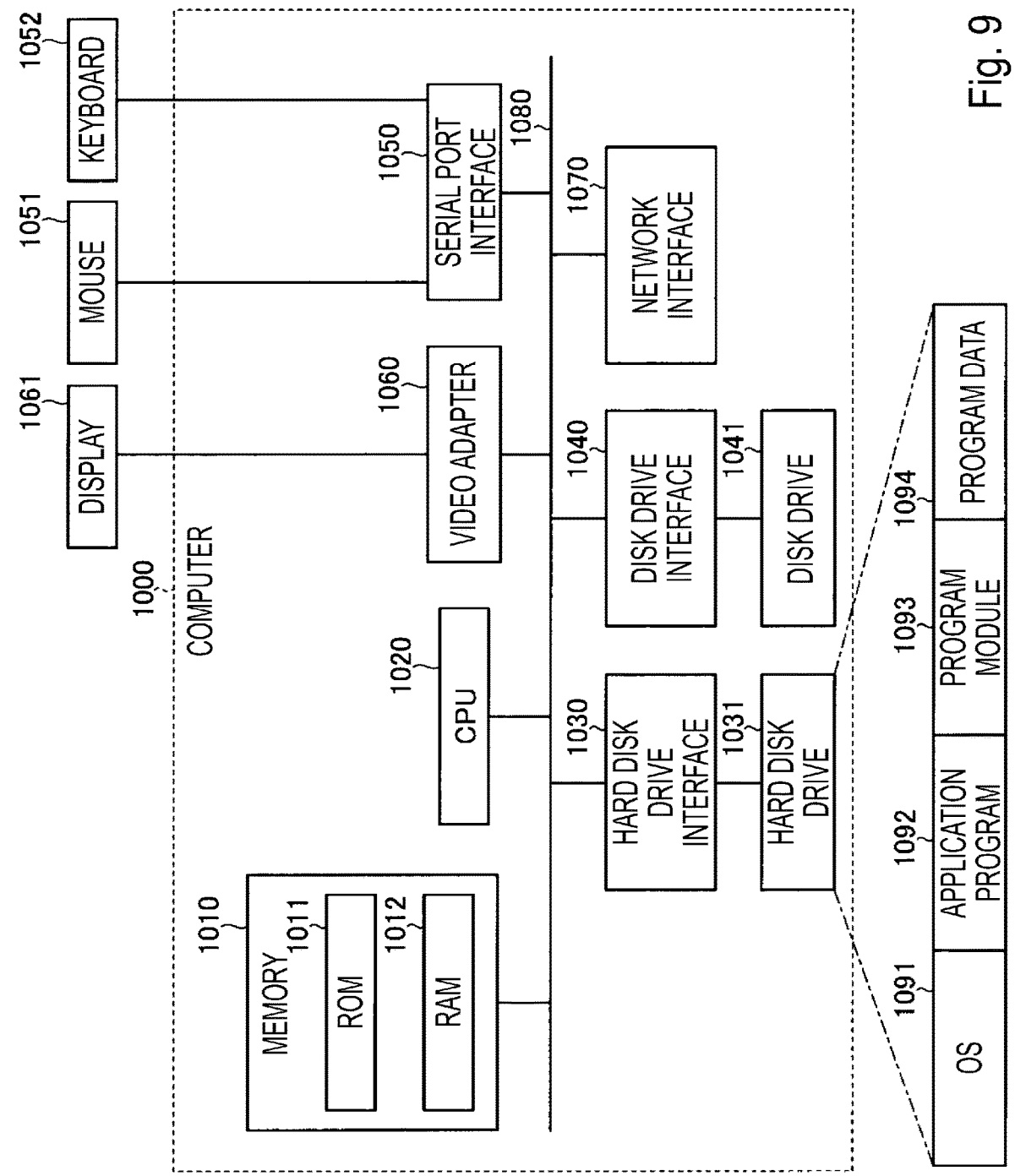
FIG. 9 is a diagram illustrating an example of a computer that executes a distance estimation program.

FIG. 9 is a diagram illustrating an example of a computer that executes the distance estimation program. A computer 1000 includes, for example, a memory 1010, a CPU 1020, a hard disk drive interface 1030, a disk drive interface 1040, a serial port interface 1050, a video adapter 1060, and a network interface 1070. These units are connected by a bus 1080.

The memory 1010 includes a read only memory (ROM) 1011 and a RAM 1012. The ROM 1011 stores, for example, a boot program such as a basic input output system (BIOS). The hard disk drive interface 1030 is connected to a hard disk drive 1031. The disk drive interface 1040 is connected to a disk drive 1041. For example, a detachable storage medium such as a magnetic disk or an optical disc is inserted into the disk drive 1041. For example, a mouse 1051 and a keyboard 1052 are connected to the serial port interface 1050. For example, a display 1061 is connected to the video adapter 1060.

Here, the hard disk drive 1031 stores, for example, an OS 1091, an application program 1092, a program module 1093, and program data 1094. Each piece of information described in the aforementioned embodiment is stored in, for example, the hard disk drive 1031 and the memory 1010.

Further, the distance estimation program is stored in the hard disk drive 1031 as the program module 1093 in which commands to be executed by the computer 1000 are described, for example. Specifically, the program module 1093 in which processing to be executed by the distance estimation apparatus 10 described in the aforementioned embodiment is described is stored in the hard disk drive 1031.

Also, data to be used in information processing according to the distance estimation program is stored as the program data 1094 in the hard disk drive 1031, for example. Then, the CPU 1020 reads the program module 1093 and the program data 1094 stored in the hard disk drive 1031 into the RAM 1012 as needed and executes each of the aforementioned procedures.

Note that the program module 1093 and the program data 1094 related to the distance estimation program are not limited to the case in which they are stored in the hard disk drive 1031, and for example, the program module 1093 and the program data 1094 may be stored in a detachable storage medium and read by the CPU 1020 via the disk drive 1041 or the like. Alternatively, the program module 1093 or the program data 1094 related to the distance estimation program may be stored in another computer connected via a network such as a LAN or a wide area network (WAN) and read by the CPU 1020 via the network interface 1070.

Although the embodiment to which the invention made by the present inventors is applied has been described above, the present invention is not limited by the description and the drawings constituting a part of the disclosure of the present invention according to the present embodiment. In other words, all of other embodiments, examples, operation technologies, and the like made by those skilled in the art based on the present embodiment fall within the scope of the present invention.

REFERENCE SIGNS LIST

10 Distance estimation apparatus
11 Input unit
12 Output unit
13 Communication control unit
14 Storage unit
15 Control unit
15a Acquisition unit
15b Estimation unit
16 Sensor
16a Acceleration sensor
16b Rotation amount sensor
16c Ocular potential meter

The invention claimed is:

1. A distance estimation apparatus comprising:
processing circuitry configured to:
acquire a sensor value output from a sensor configured to measure a relative motion of a head including an acceleration of the head or an amount of rotation of the head, or a relative motion of eyeballs of a user who visually searches for a target on a plane, the relative motion of eyeballs including an ocular potential;
estimate a size of a search target plane in field of view of the user based on a maximum value of an amount of change when a rate of change in the sensor value becomes maximum, the sensor value being acquired within a time period that is equal to or greater than a predetermined threshold; and
estimate a distance between the user and the search target plane of the target based on the size of the search target plane in field of view.

2. The distance estimation apparatus according to claim 1, wherein the processing circuitry is further configured to perform estimation using a value related to a searching action of the user from among the sensor value.

3. The distance estimation apparatus according to claim 1,
wherein the sensor is configured measure the relative motions of the head and the eyeballs, and
the processing circuitry is further configured to estimate the distance by different processing methods in accordance with whether there is a relative motion of the head or whether the relative motion of the head precedes a relative motion of the eyeballs in a relative motion corresponding to the maximum value.

4. The distance estimation apparatus according to claim 3,
wherein in a case in which there is the relative motion of the head, and the relative motion of the head precedes the relative motion of the eyeballs in the relative motion corresponding to the maximum value, the processing circuitry is further configured to estimate the distance using a total value of a sensor value of the relative motion of the head and a sensor value of the relative motion of the eyeballs,
in a case in which there is the relative motion of the head, and the relative motion of the head does not precede the relative motion of the eyeballs, the processing circuitry is further configured to estimate the distance using an average value obtained by applying predetermined weights to the sensor value of the relative motion of the head and the sensor value of the relative motion of the eyeballs, and
in a case in which there is no relative motion of the head, the processing circuitry is further configured to estimate the distance using the sensor value of the relative motion of the eyeballs.

5. A distance estimation method executed by a distance estimation apparatus, the distance estimation method comprising:
acquiring a sensor value output from a sensor configured to measure a relative motion of a head including an acceleration of the head or an amount of rotation of the head, or a relative motion of eyeballs of a user who visually searches for a target on a plane, the relative motion of eyeballs including an ocular potential;
estimating a size of a search target plane in field of view of the user based on a maximum value of an amount of change when a rate of change in the sensor value becomes maximum, the sensor value being acquired within a time period that is equal to or greater than a predetermined threshold; and
estimating a distance between the user and the search target plane of the target based on the size of the search target plane in field of view.

6. The distance estimation method according to claim 5, further comprising performing estimation using a value related to a searching action of the user from among the sensor value.

7. The distance estimation method according to claim 5, wherein acquiring the sensor value comprises measuring the relative motions of the head and the eyeballs, and
wherein estimating the distance comprises estimating the distance by different processing methods in accordance with whether there is a relative motion of the head or whether the relative motion of the head precedes a relative motion of the eyeballs in a relative motion corresponding to the maximum value.

8. The distance estimation method according to claim 7, wherein, in a case in which there is the relative motion of the head, and the relative motion of the head precedes the relative motion of the eyeballs in the relative motion corresponding to the maximum value, estimating the distance comprises estimating the distance using a total value of a sensor value of the relative motion of the head and a sensor value of the relative motion of the eyeballs,
in a case in which there is the relative motion of the head, and the relative motion of the head does not precede the relative motion of the eyeballs, estimating the distance comprises estimating the distance using an average value obtained by applying predetermined weights to the sensor value of the relative motion of the head and the sensor value of the relative motion of the eyeballs, and
in a case in which there is no relative motion of the head, estimating the distance comprises estimating the distance using the sensor value of the relative motion of the eyeballs.

9. A non-transitory computer-readable recording medium storing therein a distance estimation program that causes a computer to execute a process comprising:
acquiring a sensor value output from a sensor configured to measure a relative motion of a head including an acceleration of the head or an amount of rotation of the head, or a relative motion of eyeballs of a user who visually searches for a target on a plane, the relative motion of eyeballs including an ocular potential;
estimating a size of a search target plane in field of view of the user based on a maximum value of an amount of change when a rate of change in the sensor value becomes maximum, the sensor value being acquired within a time period that is equal to or greater than a predetermined threshold; and
estimating a distance between the user and the search target plane of the target based on the size of the search target plane in field of view.

10. The non-transitory computer-readable recording medium according to claim 9, wherein the process further comprises performing estimation using a value related to a searching action of the user from among the sensor value.

11. The non-transitory computer-readable recording medium according to claim 9,
wherein acquiring the sensor value comprises measuring the relative motions of the head and the eyeballs, and
wherein estimating the distance comprises estimating the distance by different processing methods in accordance with whether there is a relative motion of the head or whether the relative motion of the head precedes a relative motion of the eyeballs in a relative motion corresponding to the maximum value.

12. The non-transitory computer-readable recording medium according to claim 11,
wherein, in a case in which there is the relative motion of the head, and the relative motion of the head precedes the relative motion of the eyeballs in the relative motion corresponding to the maximum value, estimating the distance comprises estimating the distance using a total value of a sensor value of the relative motion of the head and a sensor value of the relative motion of the eyeballs,
in a case in which there is the relative motion of the head, and the relative motion of the head does not precede the relative motion of the eyeballs, estimating the distance comprises estimating the distance using an average value obtained by applying predetermined weights to the sensor value of the relative motion of the head and the sensor value of the relative motion of the eyeballs, and
in a case in which there is no relative motion of the head, estimating the distance comprises estimating the distance using the sensor value of the relative motion of the eyeballs.

* * * * *